United States Patent
Mallory et al.

[11] Patent Number: 6,099,708
[45] Date of Patent: Aug. 8, 2000

[54] THREE-ELECTRODE ELECTROCHEMICAL GAS SENSOR

[75] Inventors: John Mallory, Mississauga; Wenfeng Peng, North York, both of Canada

[73] Assignee: Senco Sensors, Inc., Vancouver, Canada

[21] Appl. No.: 09/149,607

[22] Filed: Sep. 8, 1998

[30] Foreign Application Priority Data

Sep. 11, 1997 [CA] Canada ................... 2215108
Aug. 14, 1998 [CA] Canada ................... 2245050

[51] Int. Cl.⁷ .................................. G01N 27/404
[52] U.S. Cl. ................... 204/412; 204/415; 204/432; 205/783
[58] Field of Search ................... 204/412, 415, 204/431, 432

[56] References Cited

U.S. PATENT DOCUMENTS

| | | | |
|---|---|---|---|
| 3,029,576 | 4/1962 | Collins ........................ | 55/68 |
| 3,429,796 | 2/1969 | Lauer ........................ | 204/195 |
| 3,668,101 | 6/1972 | Bergman ........................ | 204/195 |
| 3,755,125 | 8/1973 | Shaw et al. . | |
| 4,025,412 | 5/1977 | LaConti . | |
| 4,141,800 | 2/1979 | Breuer et al. ........................ | 204/1 T |
| 4,169,779 | 10/1979 | Tataria et al. ........................ | 204/195 |
| 4,227,984 | 10/1980 | Dempsey et al. . | |
| 4,394,239 | 7/1983 | Kitzelmann et al. . | |
| 4,406,770 | 9/1983 | Chan et al. ........................ | 204/406 |
| 4,522,690 | 6/1985 | Venkatasetty . | |
| 4,543,273 | 9/1985 | Handa . | |
| 4,587,003 | 5/1986 | Tantram et al. ........................ | 204/412 |
| 4,633,704 | 1/1987 | Tantram et al. ........................ | 73/23 |
| 5,024,682 | 6/1991 | Turk ........................ | 55/73 |
| 5,173,166 | 12/1992 | Tomantschger . | |
| 5,284,566 | 2/1994 | Cuomo et al. ........................ | 204/412 |
| 5,302,274 | 4/1994 | Tomantschger et al. ........................ | 204/412 |
| 5,338,429 | 8/1994 | Jolson et al. ........................ | 204/415 |
| 5,338,529 | 8/1994 | Pirkle et al. . | |
| 5,372,696 | 12/1994 | Kiesele et al. ........................ | 204/415 |
| 5,395,507 | 3/1995 | Aston et al. ........................ | 204/415 |
| 5,628,890 | 5/1997 | Carter et al. ........................ | 204/403 |
| 5,635,627 | 6/1997 | Bytyn ........................ | 204/415 |
| 5,656,069 | 8/1997 | Nikolskaja et al. ........................ | 96/4 |

FOREIGN PATENT DOCUMENTS

| | | |
|---|---|---|
| 0 293 230 | 11/1988 | European Pat. Off. . |
| 0762116 A1 | 3/1997 | European Pat. Off. . |
| WO 96/14576 | 5/1996 | WIPO . |

*Primary Examiner*—T. Tung
*Attorney, Agent, or Firm*—Libert & Associates; Victor E. Libert

[57] ABSTRACT

A simple, reliable, and leak-proof three-electrode electrochemical sensor for detection of toxic gases. The sensor comprises a housing having an electrochemical gas sensor cell with an electrolyte and sensing, counter and reference electrodes bonded to conductive plastic. Each of the electrodes is a membrane formed from a fluoropolymer film having a layer adhered thereto of a fluoropolymer-impregnated catalyst. The layers of each of the electrodes are bonded to conductive plastic, and are separated by an absorbent material having an electrolyte absorbed therein. The sensor is particularly intended for detection of carbon monoxide, but may be used to detect other gases.

20 Claims, 2 Drawing Sheets

THREE-ELECTRODE ELECTROCHEMICAL GAS SENSOR

FIELD OF THE INVENTION

The present invention relates to a three-electrode electrochemical gas sensor, especially a three-electrode electrochemical gas sensor used in the monitoring of the presence of a gas in an atmosphere that might contain the gas e.g. the presence of the gas in air. In preferred embodiments, the gas is carbon monoxide, but the sensor may be used to detect other gases, as described below. Nonetheless, the invention will be described herein with particular reference to detection of carbon monoxide.

BACKGROUND OF THE INVENTION

There are three principal methods of detecting the presence of carbon monoxide (CO) in air. The first method of detection uses a plug-in detector having a periodically-heated semi-conductor that exhibits a change in conductivity when CO is present. However, this type of detector requires AC-power, and ceases to function when electricity to the unit fails. The detector tends to be sensitive to changes in humidity, and is cross-sensitive to the presence of other combustible gases e.g. alcohols, including materials containing alcohols, examples of which include hairspray.

The second type of detector uses a translucent gel disk that darkens on prolonged exposure to CO. The change in translucency is detected by an infrared sensor within the unit. Detection tends to be less responsive than for other detectors, taking hours rather than minutes to recover after the ambient air has become free of CO. Consequently, it becomes necessary to remove the battery-sensor pack in order to silence the alarm that sounds when CO is detected. In addition, the gel tends to accumulate CO over a period of time, resulting in a tendency for false alarms after prolonged exposure to urban pollution.

The third type of detector uses a fuel-cell type electrochemical sensor. These detectors are battery-powered and are much more accurate and responsive to the presence of CO.

The electrolytic cell of an electrochemical sensor must have at least two electrodes. One electrode is the electrode that comes in contact with the gas that is to be detected, and is usually referred to as the sensing electrode. A second electrode is known as the counter electrode or auxiliary electrode. When the gas to be detected comes in contact with the sensing electrode, an oxidation or reduction reaction takes place at the sensing electrode, with a corresponding reduction or oxidation reaction occurring at the counter electrode.

In order to detect CO, the potential of the sensing electrode must be sufficiently positive so that CO will be oxidized. However, the potential of the sensing electrode is subject to change, because the use of a fixed external voltage bias inter-relates the potential of the sensing electrode to the potential of the counter electrode. The potential of the counter electrode is unstable if the electrode material is not electrochemically reversible, i.e. its exchange current is not high enough compared with the current passing through the cell. Consequently, it is possible that the potential of the sensing electrode will shift to a value where CO is not fully oxidised at the sensing electrode.

Thus, it can be important to have an electrode with a constant or almost constant potential throughout the reaction. Such an electrode is called the reference electrode and its main role is to stabilize the potential of the sensing electrode. In that event, the potential of the sensing electrode will remain relatively stable so that CO may be quantitatively oxidized.

An example of a two-electrode sensor is described in U.S. Pat. No. 3,755,125 and examples of three-electrode sensors are described in U.S. Pat. Nos. 4,587,003, 5,284,566 and 5,338,429. In all of these sensors, a platinum/air/water electrode was used as reference electrode. However, such sensors have a number of disadvantages, including (a) high cost due to the use of precious metals e.g. platinum foils and wires, (b) the requirement of strict performance criteria in contact between electrodes and precious metals, and high failure rates due to poor contact, (c) leakage of electrolyte through the interface of metal and plastic housing when subjected to temperature shock or after long periods of operation, (d) costs of assembly of numerous parts of the sensor, and (e) large piece-to-piece variations in sensor output.

SUMMARY OF THE INVENTION

An improved three-electrode electrochemical gas sensor for the detection of Co and other gases has now been found.

Accordingly, an aspect of the present invention provides a three-electrode electrochemical sensor for detection of a gas in an atmosphere containing the gas, said sensor comprising a housing having an electrochemical gas sensor cell with an electrolyte and three electrodes bonded to conductive plastic, said electrodes being a sensing electrode, a reference electrode and a counter electrode, said electrodes being in an aligned, spaced apart, parallel relationship with the reference electrode located between the sensing and counter electrodes and separated therefrom by an electrically-insulating material, said reference electrode having a central orifice, each of said electrodes being a membrane formed from a fluoropolymer film having a layer adhered thereto of a fluoropolymer-impregnated catalyst, said layers of each of said electrodes being bonded to conductive plastic, said layers of said electrodes being separated by absorbent material having an electrolyte absorbed therein, the absorbent material on opposed sides of the reference electrode being in contact through said orifice, the conductive plastic bonded to said electrodes being connected to means for detection of current passing through said electrodes.

Another aspect of the present invention provides a three-electrode electrochemical sensor for detection of a gas in an atmosphere containing the gas, said sensor comprising a housing having an electrochemical gas sensor cell with an electrolyte and three electrodes bonded to conductive plastic, said electrodes being a sensing electrode, a reference electrode and a counter electrode, said electrodes being in an aligned, spaced apart, parallel relationship with the reference electrode located between the sensing and counter electrodes and separated therefrom by electrically-insulating material, said reference electrode having a central orifice, each of said electrodes being a membrane formed from a fluoropolymer film having a layer adhered thereto of a fluoropolymer-impregnated catalyst, said layers of each of said electrodes being bonded to conductive plastic, said layers of said electrodes being separated by absorbent material having an electrolyte absorbed therein, the absorbent material on opposed sides of the reference electrode being in contact through said orifice, the conductive plastic bonded to said electrodes being connected to means for control of the potential of the sensing electrode with respect to the reference electrode and detection of current passing through the sensing electrode.

In a preferred embodiment of the present invention, the counter electrode has a central orifice, said electrolyte extending through the orifice in the counter electrode, and said absorbent material additionally being on opposed sides of the counter electrode and in contact through the orifice therein.

In another preferred embodiment, the electrochemical sensor is located in a housing comprising said conductive plastic and said electrically insulating material.

In a further embodiment, the membrane is a gas permeable membrane or preferably a gas porous membrane.

In another embodiment, the gas is CO and the electrolyte is sulphuric acid.

In yet another embodiment, electrical connections to the conductive plastic are external to said housing, and the sensor has a leak-proof sealed housing.

In further embodiment, the housing has a chamber in fluid communication with the atmosphere, the membrane of the sensing electrode forming part of the chamber, preferably with the chamber being separated from the atmosphere by a membrane, especially a gas permeable membrane. The chamber may contain activated carbon pellets or activated carbon impregnated polypropylene or other plastic fibers.

In yet another embodiment, the electrodes are formed by depositing a mixture of platinum black powder and a suspension of a fluoropolymer on the fluoropolymer film, and sintering the mixture under pressure onto the fluoropolymer film.

In still another embodiment, the housing is formed from a polyolefin, especially polypropylene or high density polyethylene, or polyvinyl chloride, acrylonitrile-butadiene-styrene or modified polyphenylene oxide, and the conductive plastic is polyolefin, especially polypropylene or high density polyethylene, or polyvinyl chloride, acrylonitrile-butadiene-styrene or modified polyphenylene oxide, having a filler of carbon, graphite, noble or semi-noble metals.

BRIEF DESCRIPTION OF THE DRAWINGS

The present invention is illustrated by the embodiments shown in the drawings, in which.

DETAILED DESCRIPTION OF THE INVENTION

Figure 1:
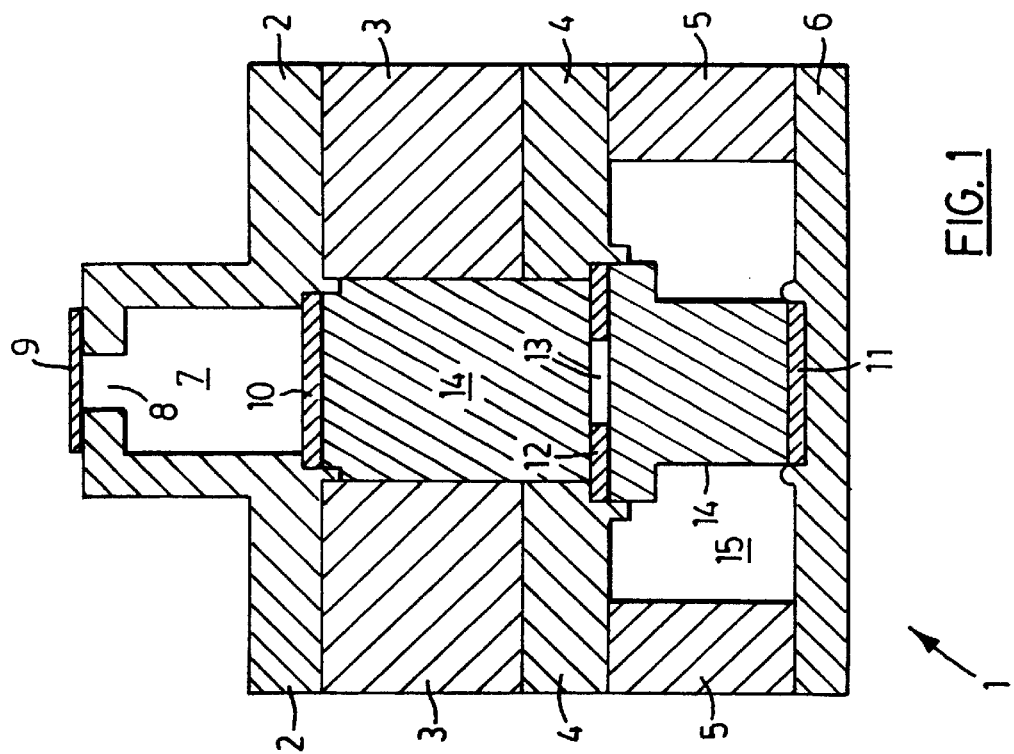
FIG. 1 is a schematic representation of a sensor of the present invention.

FIG. 1 shows a gas sensor, generally indicated by 1. Gas sensor 1 has a housing that is formed from sensing electrode current collector 2, first separator 3, reference electrode current collector 4, second separator 5 and counter electrode current collector 6. Sensing electrode current collector 2 is separated from reference electrode current collector 4 by first separator 3. Similarly, reference electrode current collector 4 is separated from counter electrode current collector 6 by second separator 5. As shown in FIG. 1, the combination of the current collectors and the separators essentially form all of the housing for gas sensor 1.

As shown in FIG. 1, sensing electrode current collector 2 extends upwardly, as viewed, and forms scrubber chamber 7. At its upper end, scrubber chamber 7 has gas passage 8 which is covered on its external side by membrane 9. Although FIG. 1 shows sensing electrode current collector 2 extending upwards to form scrubber chamber 7, it is to be understood that the extending portion of sensing electrode current collector 2 could be in the form of a cap having gas passage 8 and membrane 9.

The end of scrubber chamber 7 opposed to membrane 9 has sensing electrode 10. The construction of sensing electrode 10 is described below, but sensing electrode 10 is bonded to sensing electrode current collector 2 so that an electrical connection is formed between them. Sensing electrode 10 has a membrane with an electrode surface thereon, sensing electrode 10 being disposed such that the membrane surface thereof and not the electrode surface is disposed towards scrubber chamber 7.

Counter electrode current collector 6 has counter electrode 11 thereon. Counter electrode 11 is bonded to and forms an electrical communication with counter electrode current collector 6. Counter electrode 11 is disposed such that its electrode surface is towards sensing electrode 10.

Intermediate between sensing electrode 10 and counter electrode 11 is reference electrode 12. Reference electrode 12 is bonded to and forms an electrical connection with reference electrode current collector 4. Reference electrode 12 is shown as being an annular electrode with electrode orifice 13 therein.

The space of gas sensor 1 located between sensing electrode 10 and counter electrode 11 is filled with absorbent material 14. Absorbent material 14 would normally be in the form of two or more pads e.g. pads located between sensing electrode 10 and reference electrode 12 and between reference electrode 12 and counter electrode 11. Absorbent material 14 contains electrolyte, to form the electrochemical cell between the electrodes. Electrolyte is stored in electrolyte reservoir 15, and absorbed from electrolyte reservoir 15 by absorbent material 14. Absorbent material 14 needs to be inert with respect to the electrolyte.

Figure 2:
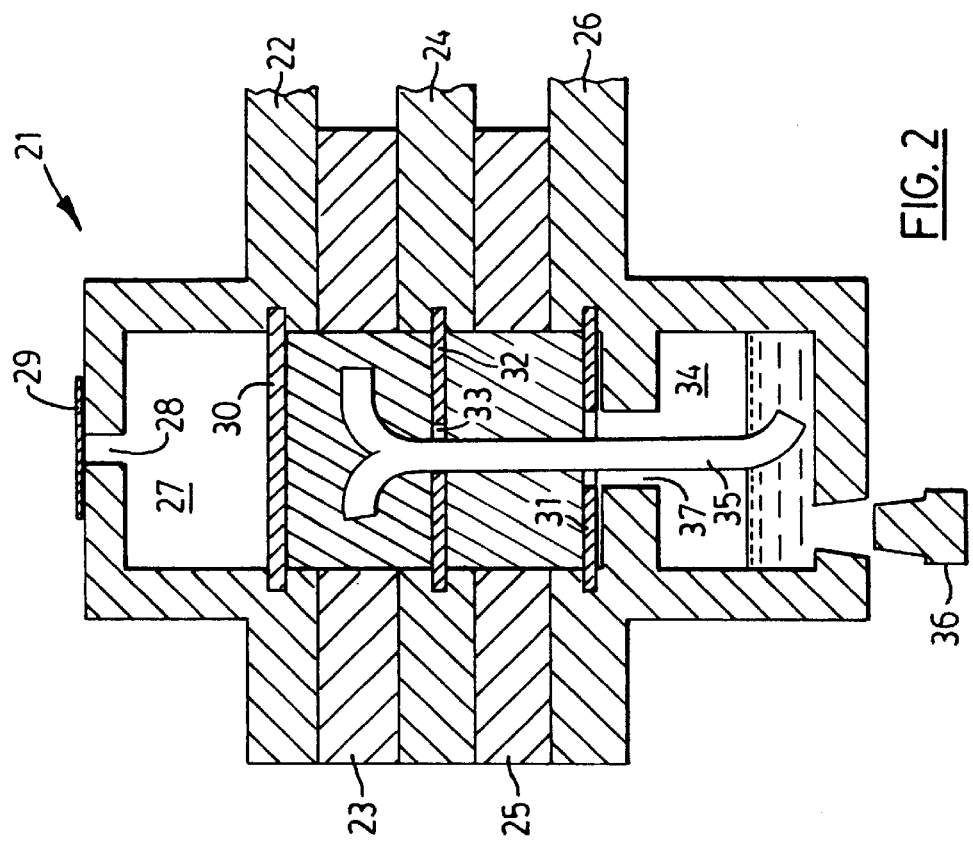
FIG. 2 is a schematic representation of another embodiment of the sensor of the present invention.

FIG. 2 shows another embodiment of the gas sensor, generally indicated by 21. Gas sensor 21 has a housing that is formed from sensing electrode current collector 22, first separator 23, reference electrode current collector 24, second separator 25 and counter electrode current collector 26. Sensing electrode current collector 22 is separated from reference electrode current collector 24 by first separator 23. Similarly, reference electrode current collector 24 is separated from counter electrode current collector 26 by second separator 25. As shown in the embodiment of FIG. 1, the combination of the current collectors and the separators essentially forms all of the housing for gas sensor 21.

As shown in FIG. 2, sensing electrode current collector 22 extends upwardly, as viewed, and forms scrubber chamber 27. At its upper end, scrubber chamber 27 has gas passage 28 which is covered on its external side by membrane 29. As in FIG. 1, it is to be understood that the extending portion of sensing electrode current collector 22 could be in the form of a cap having gas passage 28 and membrane 29.

Sensing electrode 30 is bonded to sensing electrode current collector 22 so that an electrical connection is formed between them. As previously, sensing electrode 30 has a membrane with an electrode surface thereon, sensing electrode 30 being disposed such that the membrane surface thereof and not the electrode surface is disposed towards scrubber chamber 27. Similarly, intermediate between sensing electrode 30 and counter electrode 31 is reference electrode 32. Reference electrode 32 is bonded to and forms an electrical connection with reference electrode current collector 24. Reference electrode 32 is shown as being an annular electrode with electrode orifice 33 therein.

Counter electrode 31 is bonded to and forms an electrical communication with counter electrode current collector 26. The embodiment of FIG. 2 differs from that of FIG. 1 in that, in particular, counter electrode 31 is also an annular electrode, with electrode orifice 37 therein.

The space of gas sensor 21 located beneath sensing electrode 30 and extending down through orifice 33 in reference electrode 32 and orifice 37 in counter electrode 31 into reservoir 34 contains absorbent material 35. Absorbent material may in the form of two or more pads e.g. pads located between sensing electrode 30 and reference electrode 32 and between reference electrode 32 and counter electrode 31. It is understood that the sensor preferably contains absorbent material in the form of wick 35 in addition to absorbent pads. In the embodiment shown, wick 35 extends from reservoir 34 to above reference electrode 32, at which location it is split to aid in retention in position. All absorbent material contains electrolyte, to form the electrochemical cell between the electrodes.

FIG. 2 shows plug 36 in the wall of counter electrode current collector 26 surrounding reservoir 34. Plug 36 may be used in sealing the cell after the reservoir has been filled with electrolyte.

Figure 3:
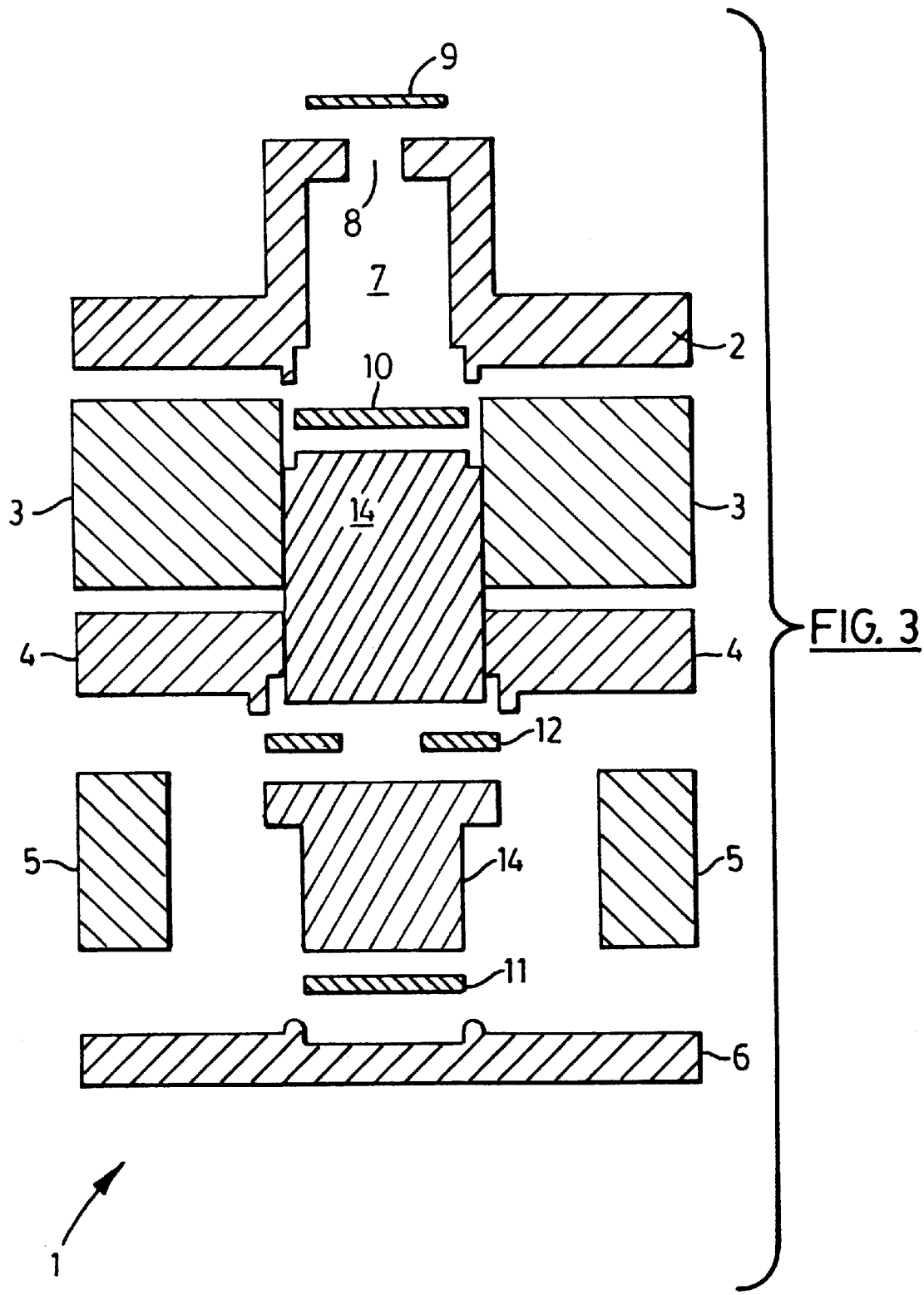
FIG. 3 is a schematic representation of an embodiment of the sensor of FIG. 1 in exploded partial cut-away form.

FIG. 3 shows gas sensor 1 of FIG. 1 in an exploded view. Sensing electrode current collector 2 has gas passage therein over which membrane 9 fits. Sensing electrode current collector 2 forms scrubber chamber 7, the lower surface of scrubber chamber 7 being formed by sensing electrode 10. Adjacent to sensing electrode current collector 2 are first separator 3, reference electrode current collector 4, second separator 5 and counter electrode current collector 6. It is to be understood that each of first separator 3, reference electrode current collector 4, and second separator 5 are annular in construction, to form a central space in the gas sensor. Absorbent material 14 is located in the annular region (space) between those current collectors and separators. Counter electrode 11 is located juxtaposed to counter electrode current collector 6. Annular reference electrode 12 is located at reference electrode current collector 4.

As discussed herein, each of the electrodes is bonded to their respective electrode current collectors. Such bonding of the electrodes to the electrode current collectors seals gas sensor 1, and in particular separates liquid electrolyte from scrubber housing 7.

The gas sensor is illustrated in FIGS. 1–3 in the preferred embodiment of being of circular cross-section. Such a cross-section permits ease of manufacture, including ease of fitting parts together and of screwing certain elements, if that should be a desirable part of the method of manufacture. The circular cross-section also results in a compact gas sensor that may easily be located in a desired location.

FIGS. 1 and 2 show two typical sensor structures of the present invention. In FIG. 1, an electrolyte reservoir is located between the reference and counter electrodes. There is an orifice in the center of the reference electrode which is filled with a small fiberglass adsorbent pad, providing pathways for electrolyte and charged ions. FIG. 2 shows an electrolyte reservoir under the counter electrode. Accordingly, there is an orifice in the center of the counter electrode. A hydrophilic wick passes the reference and counter electrodes, through the orifices, and extends to the bottom of the reservoir. The top of wick is split so that it can be securely installed in place. Alternatively, the reservoir can be incorporated in other places of the sensor cell, for convenience of assembly.

The electrolyte adsorbent matrix between electrodes is preferably partly hydrophilic and partly hydrophobic, providing pathways for ions and gases. The partly hydrophilic and partly hydrophobic matrix can be made by impregnating homogeneously a hydrophobic binder (e.g. Teflon™ fluoropolymer) into the hydrophilic absorbent material. A matrix can also be made that is locally hydrophobic. For example, a fiberglass matrix pad may be pretreated using a suspension of Teflon fluoropolymer, and dried and sintered. The pad is then rolled, and both ends are cut off so that its length is equal to the distance between two neighboring electrodes. The rolled matrix is installed in such a way that both fresh fiberglass surfaces are in contact with electrodes. Other methods include hydrophobic treatment of the inner wall of the cell, and use of hydrophobic gaskets between electrodes.

Gas sensor 1 may be fabricated in modules, which are then assembled to form the gas sensor. The various parts of the gas sensor are bonded together e.g. using ultrasonic welding, in order to effect liquid and gas tight seals to prevent leakage of liquid from the gas sensor and extraneous intrusion of gases into the sensor.

In an example of the method of manufacture, carbon pellets are placed in scrubber housing 7 and membrane 9 added, and bonded. Sensing electrode 10 is placed in sensing electrode current collector 2 and bonded thereto, preferably by ultrasonic welding. The separators, electrodes and current collectors are then sequentially added and bonded, preferably using ultrasonic welding. It is understood that the absorbent material would be added at the appropriate times. Sufficient absorbent material added to ensure that there is absorbent material between the sensing electrode and the counter electrode, including through the orifice in the reference electrode. Fluid (electrolyte) may be added to the reservoir through a plug (an example of which is shown in FIG. 2). The gas sensor is now ready for installation and connection to electronic monitoring means, as will be understood. The gas sensor, when fabricated, should be gas tight to prevent diffusion of gas, especially CO, into the sensor from a path other than the sensing electrode, as diffusion of gas affects the output of the sensor.

It is to be understood that each of the electrodes is connected to electronic controlling and measuring means exterior to the gas sensor through the current collectors. The current collectors are conductive plastics, as discussed herein, with the result that there are no wire connections from the electrodes through the housing of gas sensor 1 to the electronic monitoring means. Connections to the electronic monitoring means should be external to the gas sensor 1, being connected on the external part of each of the current collectors. This eliminates possible failure of the sensor due to corrosion of or at the location of electrical leads passing through the housing of a gas sensor to connect to the electrodes.

Although the electrodes could be of different constructions, it is preferred that each of the electrodes be of the same construction. It is preferred that the electrodes be gas porous membranes formed from a fluoropolymer film having a layer of a fluoropolymer-impregnated catalyst adhered thereto. Such an electrode may be formed by spraying or otherwise depositing e.g. by silk screen printing, a mixture of platinum black powder and a suspension of a fluoropolymer onto a fluoropolymer film. An example of a porous membrane is a Mitex™ PTFE membrane from Millipore Co. with a thickness of 125 microns, a porosity of 60% and a mean pore diameter of 5 microns, other membranes being known to those skilled in the art. Subsequently, the mixture of platinum black and fluoropolymer is sintered onto the fluoropolymer film. This may be accomplished by applying both heat and pressure to the coating of platinum black and fluoropolymer on the fluoropolymer film, so that the mixture is sintered and is strongly adhered to the film.

In examples of the electrodes, a mixture of platinum black and fluoropolymer powder in the ratio of 10:2, is coated onto a porous fluoropolymer membrane, followed by pressing and sintering. The fluoropolymer binder is hydrophobic, and creates gas passages in the electrode, and increases the physical strength of the electrode.

Electrodes made by the above method have a high electrochemical surface area. Platinum black typically has an average surface area of 25 $m^2/g$. A circular electrode with an area of 1 $cm^2$ and thickness 0.13 mm utilizes about 5.5 mg of platinum and provides a surface area of about 0.1375 $m^2$ i.e. 1375 times its apparent geometrical area, although the actual reactive surface area is smaller. The larger the reference electrode, the more stable the sensor tends to be.

Electrodes may also be made with additional binders e.g. carbon or glass fibers. These materials increase the electrochemical surface area while lowering the amount of platinum that is required. For example, a mixture of platinum and carbon powder (1:4 by weight) shows a catalytic surface area as high as 140 $m^2/g$. Glass fibers are hydrophilic and wick aqueous electrolyte into the innermost parts of the electrode by capillary action.

The resultant layer of fluoropolymer-impregnated catalyst on the fluoropolymer film is adhered directly onto the conductive plastic that forms the electrode current collectors. In the embodiments, conductive plastic is formed from a polyolefin, especially polypropylene or high density polyethylene, polyvinyl chloride, acrylonitrile-butadiene-styrene or modified polyphenylene oxide, although other materials may be used. The conductive plastic has a filler of carbon or graphite in an amount that provides electrical conductive properties to the plastic. In embodiments, the conductive plastic contains up to 40% by weight of carbon or graphite fibers, and has a specific resistance of about 10–100 ohms/cm. The electrodes may be bonded to the electrode current collectors using ultrasonic welding, although other electrical communication means of bonding the layer to the housing may be used.

A typical gas diffusion electrode contains high surface area catalysts such as platinum black and a hydrophobic binder, usually fine particles of fluoropolymer e.g. particles of Teflon™ fluoropolymer. Electron microscopic examination of the fluoropolymer-bonded platinum black electrode showed that the platinum black formed loosely packed aggregates interspersed with fluoropolymer particles and threads, the threads binding the material into a mechanically secure structure. When a hydrophilic catalyst is wetted by electrolyte, the hydrophobic binder remains dry, providing gas paths throughout the depth of the electrode. The liquid films around the catalyst particles are so thin that the gas diffusion path is greatly shortened. Hence, highly efficient gas diffusion electrodes are obtained. The loading of platinum black ranges from 1 to 20 $mg/cm^2$. The loading of fluoropolymer binder ranges from 5% to 50% by weight.

In the preferred embodiment of FIG. 1, a fluoropolymer membrane is placed across gas passage 8. The membrane, 9, which is preferably a gas permeable membrane but may be a gas porous membrane, is intended to prevent contamination of the sensor by particulates, aerosols and other organic or high molecular weight molecules as a consequence of the flow of ambient atmospheric air directly into scrubber chamber 7, evaporation of the reservoir liquid from the sensor and reduce effects of pressure fluctuations and air turbulence on the gas sensor. Use of a gas permeable membrane may increase the response time of the sensor to the presence of CO. For instance, in a test of an embodiment of a sensor using a membrane that was Teflon™ FEP fluoropolymer film with a nominal thickness of 0.5 mil and obtained from the DuPont Company, the response time increased from less than one minute to 2.5 minutes for an atmosphere with 90 ppm of CO, but tests of another membrane formed from a porous fluoropolymer film with a polycarbonate backing gave no significant increase in response time. Thus, a membrane may be selected that provides an increase in response time, if any, that is acceptable for the proposed use.

In addition, scrubber chamber 7 preferably contains pellets of carbon or activated carbon-impregnated polypropylene fibre matrix, or other absorbent, to absorb polar gases e.g. $H_2S$ and high molecular weight organic vapours in the atmospheric air and which has passed through the gas permeable membrane 9. These substances poison and degrade the sensing electrode. Membrane 9 is preferably a fluoropolymer membrane.

The sensor of the present invention uses three electrodes. However, the sensing electrode is always exposed to the ambient atmosphere, whereas the other electrodes are isolated. The reference electrode is conveniently an air/water reference electrode and its potential is governed by the redox couple of oxygen/water. Any carbon monoxide that reaches the sensor will be fully converted to carbon dioxide ($CO_2$) at the sensing electrode site. The reaction at the sensing electrode consumes water and generates an excess of hydrogen ions, which subsequently migrate to the counter electrode and are involved in the counter electrode reaction to produce an equal amount of water. The net reaction in the cell is the conversion of CO to $CO_2$ and no substance in the sensor is consumed. Thus, the sensor will not degrade after long-term exposure to CO. It is to be understood that the sensor is operational only in air or oxygen-abundant atmospheres.

The various outer parts of the housing may be fabricated from a polymer that is resistant to sulphuric acid e.g. high density polyethylene, polypropylene, acrylonitrile-butadiene-styrene (ABS), polyvinyl chloride (PVC) polyvinylidene difluoride (PVDF) and modified polyphenylene oxide, and the like. The conductive plastic may be formed from these polymers containing noble or semi-noble metals, carbon or graphite, or the like. Typical amounts of filler are 10–40% by weight, so that the overall resistance is less than 100 $\Omega \cdot cm^{-1}$. It is preferred that the separators and current collectors be made of the same plastic material, so that all parts have similar or the same properties, especially thermal parameters. This will assure that all parts are strongly bonded together, even when subjected to rapid changes in temperature. Furthermore, the filler content should not be too high, provided that there is good conductivity through the conductive parts. In a preferred embodiment, the conductive plastic contains carbon or graphite fibres.

For operation, reservoir is charged with sulphuric acid, for example 20–50% (v/v) $H_2SO_4$ aqueous electrolyte solution, during assembly of gas sensor 1, although a wide range of concentrations may be used e.g. a range of at least 10–75% (v/v) $H_2SO_4$. The reservoir is preferably loosely packed with an inert material, for instance fibreglass wool, to reduce "sloshing" of liquid in the reservoir during movement of the sensor. Gas sensor 1 is then placed in the location where carbon monoxide is to be monitored, and connected to electronic monitoring means for detection of currents flowing through the electrodes, as will be understood by persons skilled in the art. In the absence of carbon monoxide, the current should be null. When the atmosphere contains carbon monoxide, carbon monoxide permeates through membrane 9 and comes in contact with sensing electrode 10, being oxidised at the sensing electrode and correspondingly producing a current, which is amplified by external electronic means. A microcomputer will then compare this signal to a pre-set reference level to determine whether an alarm signal should be issued.

The gas sensor is described herein with particular reference to detection of carbon monoxide. However, it is to be understood that the sensor may be used to detect other gases e.g. hydrogen sulphide ($H_2S$), oxides of nitrogen (NO and $NO_2$), sulphur dioxide ($SO_2$), chlorine, alcohol and the like. For detection of a specific gas other than carbon monoxide, it might be necessary to remove or replace the scrubber (carbon, pellets) described herein, change the electrode composition and/or set the voltage bias at a different value, as will be understood by persons skilled in the art.

In an example of an embodiment of the sensor of the invention, the sensor, reference and counter electrodes had an exposed area of 8–15 mm in diameter. The reference and/or counter electrode had an orifice with a diameter of 3–5 mm.

The present invention is illustrated by the following examples.

EXAMPLE I

A sensor of the invention was connected to a EG&G Princeton Applied Research Model 263 potentiostat/Galvanostat. The working electrode lead of the instrument was connected to the sensing electrode, and the counter and reference electrode leads of the instrument to the respective electrodes. The instrument was set to potentiostat mode and the potential was set to 0.000 V. Sensor responses to carbon monoxide were recorded on a BAS (Bioanalytical Systems) XYT chart recorder.

The sensor was placed in a glass bell jar containing clean air.

A series of tests were conducted to assess the sensitivity, response rate, stability and influence of temperature in the detection of carbon monoxide.

The sensor was found to give a linear response to concentrations of carbon monoxide (CO) in air over a range of concentration of from 0–10% (v/v). Typical sensor output at 20° C. was 25 nA/ppm. The lower detection limit was found to be 1 ppm.

When stabilized in clean air, the sensor output current was within ±0.1 $\mu A$.

The sensor responded instantly to the presence of CO. With air containing 100 ppm of CO, the output current of the sensor reached 90% of full scale within 2 minutes.

The output of the sensor remained unchanged when exposed to 400 ppm of CO for more than 20 hours.

The background current was not affected by temperature changes in the range of −10° C. to 45° C. However, the sensor response to a given concentration of CO increased with temperature.

The gas sensor of the present invention provides for monitoring of the presence of a number of gases, especially CO, using a compact sealed sensor that is not susceptible to adverse affects of wires passing through the housing of the sensor. The invention also provides a cost effective and more reliable sensor for the toxic gas detector market. The sensor is particularly intended for domestic use in monitoring low levels of carbon monoxide, but it may be used in other uses. The electrode configuration especially used with an activated carbon filter, simplifies the sensor design and makes possible the use of conductive plastics instead of platinum as current collector. It is also believed that the sensor is superior to other models in terms of life and reliability.

In contrast, known sensors with metal pins usually have precious platinum wires/foils spot-welded to make contact with electrodes, as a consequence of the nature of the electrolyte that is used. These wires or foils tend to be so thin that a good electrical connection cannot be guaranteed, and the connection tends to be vulnerable and fragile, too. In addition, because metals and plastics have totally different heat expansion coefficients, such sensors tend to leak electrolyte after exposure to significantly different temperatures and be contaminated by metals that are dissolved in the electrolyte. The contamination and leakage of electrolytes can significantly affect sensor performance and shorten the sensor life. It is believed that these problems have been avoided or alleviated in the sensor of the invention.

What is claimed is:

1. A three-electrode electrochemical sensor for detection of a gas in an atmosphere containing the gas, said sensor comprising a housing having an electrochemical gas sensor cell with an electrolyte and three electrodes bonded to conductive plastic, said electrodes being a sensing electrode, a reference electrode and a counter electrode, said electrodes being in an aligned, spaced apart, parallel relationship with the reference electrode located between the sensing and counter electrodes and separated therefrom by an electrically-insulating material, said reference electrode having a central orifice, each of said electrodes being a membrane formed from a fluoropolymer film having a layer adhered thereto of a fluoropolymer-impregnated catalyst, each of said layers of said electrodes being ultrasonically welded to conductive plastic, said layers of said electrodes being separated by absorbent material having an electrolyte absorbed therein, the absorbent material on opposed sides of the reference electrode being in contact through said orifice, the absorbent material between electrodes being partly hydrophilic and partly hydrophobic, the conductive plastic ultrasonically welded to said electrodes being connected to electrical connection means for detection of current passing through said electrodes, said housing being a leak-proof sealed housing and the electrical connection means connected to said conductive plastic being external to said housing.

2. The apparatus of claim 1 in which the counter electrode has a central orifice, said electrolyte extending through the orifice in the counter electrode, and said absorbent material additionally being on opposed sides of the counter electrode and in contact through the orifice therein.

3. The apparatus of claim 2 in which a wick extends through the orifice in each of the reference and counter electrodes.

4. The apparatus of claim 1 in which each of the electrodes is a gas permeable membrane.

5. The apparatus of claim 1 in which each of the electrodes is a porous membrane.

6. The apparatus of claim 1 in which the housing has a chamber in fluid communication with the atmosphere, said membrane of said sensing electrode forming part of the chamber.

7. The apparatus of claim 6 in which said chamber is separated from the atmosphere by a membrane.

8. The apparatus of claim 7 in which said chamber is separated from the atmosphere by a gas permeable membrane.

9. The apparatus of claim 6 in which the chamber is filled with an absorbent for gases in the atmosphere that are poisonous to the electrode.

10. The apparatus of claim 6 in which the chamber contains carbon pellets or carbon impregnated polymer fibre matrix.

11. The apparatus of claim 1 in which the electrodes are formed by depositing a mixture of platinum black powder and a suspension of a fluoropolymer on the fluoropolymer film, and sintering the mixture under pressure onto the fluoropolymer film.

12. The apparatus of claim 11 in which the housing is formed from a polymer selected from polyolefin, polyvinyl chloride, modified polyphenylene oxide or acrylonitrile-butadiene-styrene copolymer.

13. The apparatus of claim 12 in which the conductive plastic is formed from a polymer selected from polyolefin, polyvinyl chloride, modified polyphenylene oxide or acrylonitrile-butadiene-styrene copolymer.

14. The apparatus of claim 1 in which the housing and conductive polymer are formed from polyolefin, and said polyolefin is polypropylene or high density polyethylene.

15. The apparatus of claim 1 in which the conductive plastic has a filler of carbon, graphite, or noble or semi-noble metals.

16. The apparatus of claim 1 in which the gas to be detected is carbon monoxide.

17. The apparatus of claim 1 in which the catalyst is platinum and the electrolyte is aqueous sulphuric acid solution.

18. The apparatus of claim 1 in which the housing is formed from polypropylene and the conductive plastic is polypropylene having a filler of carbon fibres.

19. The apparatus of claim 1 in which the electrochemical sensor is located in a housing comprising said conductive plastic and said electrically insulating material.

20. The apparatus of claim 1 in which the conductive plastic bonded to said electrodes is connected to means for control of the potential of the sensing electrode with respect to the reference electrode.

* * * * *